(12) United States Patent
Maskara et al.

(10) Patent No.: US 9,031,647 B2
(45) Date of Patent: May 12, 2015

(54) GUIDEWIRE AND SIGNAL ANALYZER FOR PACING SITE OPTIMIZATION

(75) Inventors: Barun Maskara, Blaine, MN (US);
Yinghong Yu, Shoreview, MN (US);
Bruce A. Tockman, Scandia, MN (US);
Sunipa Saha, Shoreview, MN (US);
Martin McDaniel, San Diego, CA (US);
Geng Zhang, Newbury Park, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 650 days.

(21) Appl. No.: 13/293,707

(22) Filed: Nov. 10, 2011

(65) Prior Publication Data

US 2012/0130220 A1    May 24, 2012

Related U.S. Application Data

(60) Provisional application No. 61/415,221, filed on Nov. 18, 2010.

(51) Int. Cl.
*A61N 1/05* (2006.01)
*A61B 5/0472* (2006.01)
(Continued)

(52) U.S. Cl.
CPC ............. *A61N 1/056* (2013.01); *A61N 1/37241* (2013.01); *A61N 2001/0585* (2013.01); *A61B 5/042* (2013.01); *A61B 5/0422* (2013.01); *A61B 5/0472* (2013.01); *A61B 5/6851* (2013.01)

(58) Field of Classification Search
CPC .... A61B 5/042; A61B 5/0452; A61B 5/6869; A61B 5/6851; A61B 5/06; A61B 5/065; A61B 5/068; A61B 2017/00022; A61B 2017/00026; A61B 2017/00044; A61B 2017/00243; A61N 1/056; A61N 1/0563; A61N 1/39; A61N 1/3956; A61N 1/3962; A61N 1/362; A61N 1/37241; A61N 1/3684; A61N 1/3686; A61N 2001/0585
USPC .......... 600/374, 509, 510; 607/4, 5, 9, 27, 28, 607/122; 128/898
See application file for complete search history.

(56) References Cited

U.S. PATENT DOCUMENTS

| 5,957,842 A | 9/1999 | Littmann et al. |
| 6,351,673 B1 | 2/2002 | Ding et al. |

(Continued)

FOREIGN PATENT DOCUMENTS

| JP | 2003024447 A | 1/2003 |
| JP | 2008534165 A | 8/2008 |

(Continued)

OTHER PUBLICATIONS

International Search Report and Written Opinion issued in PCT/US2011/060165, mailed Apr. 2, 2012, 14 pages.

*Primary Examiner* — Lee S Cohen
*Assistant Examiner* — Erin M Cardinal
(74) *Attorney, Agent, or Firm* — Faegre Baker Daniels LLP

(57) ABSTRACT

Cardiac lead implantation systems, devices, and methods for lead implantation are disclosed. An illustrative cardiac lead implantation system comprises a mapping guidewire including one or more electrodes configured for sensing cardiac electrical activity, a signal analyzer including an analysis module configured for analyzing an electrocardiogram signal sensed by the mapping guidewire, and a user interface configured for monitoring one or more hemodynamic parameters within the body. The sensed electrical activity signal can be used by the analysis module to compute a timing interval associated with ventricular depolarization.

16 Claims, 11 Drawing Sheets

(51) Int. Cl.
*A61B 5/00* (2006.01)
*A61N 1/372* (2006.01)
*A61B 5/042* (2006.01)

(56) References Cited

U.S. PATENT DOCUMENTS

| | | |
|---|---|---|
| 6,360,127 B1 | 3/2002 | Ding et al. |
| 6,453,192 B1 | 9/2002 | Ding et al. |
| 6,542,775 B2 | 4/2003 | Ding et al. |
| 6,684,103 B2 | 1/2004 | Ding et al. |
| 6,923,772 B2 | 8/2005 | Yu et al. |
| 6,993,389 B2 * | 1/2006 | Ding et al. .................. 607/25 |
| 7,113,823 B2 | 9/2006 | Yonce et al. |
| 7,142,922 B2 | 11/2006 | Spinelli et al. |
| 7,347,751 B2 | 3/2008 | Sweeney et al. |
| 7,630,764 B2 | 12/2009 | Ding et al. |
| 7,751,882 B1 * | 7/2010 | Helland .......................... 607/9 |
| 2002/0143264 A1 | 10/2002 | Ding et al. |
| 2003/0028128 A1 | 2/2003 | Tenerz |
| 2004/0024425 A1 | 2/2004 | Worley et al. |
| 2005/0165324 A1 * | 7/2005 | Receveur et al. ............ 600/549 |
| 2005/0216065 A1 | 9/2005 | Ding et al. |
| 2006/0069419 A1 | 3/2006 | Sweeney et al. |
| 2007/0173861 A1 * | 7/2007 | Strommer et al. ............ 606/108 |
| 2007/0233215 A1 * | 10/2007 | Sommer et al. ................ 607/122 |
| 2008/0177344 A1 | 7/2008 | Maskara et al. |
| 2008/0243195 A1 | 10/2008 | Sommer et al. |
| 2009/0157136 A1 | 6/2009 | Yang et al. |
| 2010/0152801 A1 | 6/2010 | Koh et al. |
| 2011/0264038 A1 | 10/2011 | Fujimoto et al. |

FOREIGN PATENT DOCUMENTS

| | | |
|---|---|---|
| JP | 2010094235 A | 4/2010 |
| JP | 2010534549 A | 11/2010 |
| WO | WO9509561 A1 | 4/1995 |
| WO | WO9526678 A1 | 10/1995 |
| WO | WO2006105474 A2 | 5/2006 |
| WO | WO2009020639 A1 | 2/2009 |

* cited by examiner

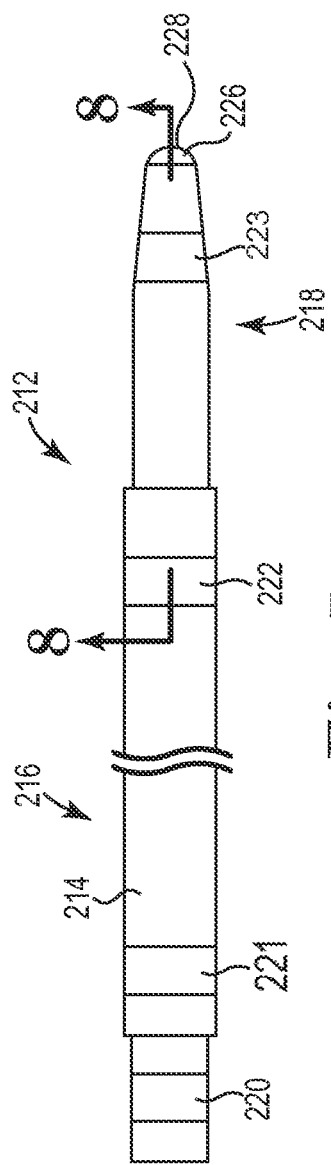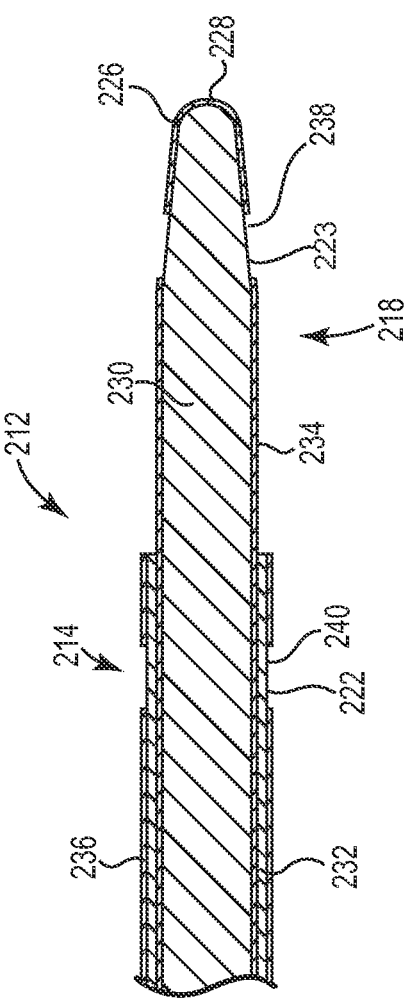

GUIDEWIRE AND SIGNAL ANALYZER FOR PACING SITE OPTIMIZATION

CROSS-REFERENCE TO RELATED APPLICATION

This application claims priority to U.S. Provisional Application Ser. No. 61/415,221, filed Nov. 18, 2010, the contents of which are incorporated herein by reference in their entirety for all purposes.

TECHNICAL FIELD

The present invention relates generally to implantable medical devices. More specifically, the present invention pertains to cardiac lead implantation systems, devices, and methods for lead implantation.

BACKGROUND

Cardiac rhythm management devices are used for providing pacing stimulation to one or more heart chambers in an attempt to improve the rhythm and coordination of atrial and/or ventricular contractions. In cardiac resynchronization therapy (CRT), for example, a number of leads are typically delivered transvenously into or near the heart and include a number of lead electrodes that contact the myocardium for sensing cardiac electrical activity and for delivering electrical stimulation therapy to the heart. Some cardiac pacemakers are capable of delivering CRT therapy by pacing multiple heart chambers. In some techniques, for example, pacing pulses are delivered to multiple heart chambers in a sequence that causes the heart chambers to contract in synchrony, increasing the pumping power and efficiency of the heart. In the case of dysynchrony of the right and left ventricular contractions, for example, biventricular pacing therapy may be used to pace one or both of the ventricles to increase cardiac output. In other techniques, biatrial pacing or pacing of all four heart chambers may be performed to increase cardiac output.

Lead delivery in CRT applications typically involves the delivery of multiple leads to different target pacing sites in or near the heart. In some applications, this process may involve the manipulation of a lead through the coronary sinus and into a branch cardiac vessel located adjacent to the left side of the heart such as a middle branch cardiac vein or posterior branch cardiac vein. Typically, the clinician must manipulate the lead to a target pacing site in or near the heart and, once in place at the site, connect a number of electrical clips to the lead to enable various sensing and impedance measurements to be taken via a pacing system analyzer (PSA) or programming device. In some cases, the implantation of the lead is performed using a venogram by injecting a contrast dye into the patient's blood stream and then determining, for that specific patient, which branch vessel to select using a fluoroscopic monitor.

Lead placement for CRT applications is often accomplished by an iterative trial and error process, in many cases requiring the clinician to manipulate the lead and test the efficacy of the pacing site multiple times before a suitable location is found. The selection of the lead pacing site can have a significant impact on the hemodynamic response to CRT therapy. Consequently, to determine an appropriate pacing site, some CRT implantation techniques involve measuring various timing intervals between each implanted lead electrode and a reference point such as another lead electrode located within the body or a surface EKG electrode. In a biventricular synchronization system in which left ventricular pacing therapy is to be provided, for example, a timing interval between first and second features associated with left ventricular depolarization (e.g., Q-LV or Q1-LV) may be computed for each proposed left ventricular pacing site that results in activation. Based on the timing intervals associated with the patient's responsiveness to CRT, the clinician may then determine the selection of a site based on the location of the latest activation. Other factors such as the size of the vessel and the ease of implanting the lead at the target site may also be considered by the clinician in determining the selection of a site for lead implantation.

SUMMARY

The present invention pertains to cardiac lead implantation systems, devices, and methods for lead implantation. In Example 1, a cardiac lead implantation system comprises a mapping guidewire having a proximal section and a distal section, the distal section including at least one electrode configured to sense cardiac electrical activity within the body; a signal analyzer including an analysis module configured for analyzing an electrocardiogram activity signal sensed by the mapping guidewire, wherein the signal analyzer is configured to determine a timing interval associated with ventricular depolarization based at least in part on the sensed electrocardiogram activity signal; and a user interface configured for monitoring timing intervals within the body.

In Example 2, the system of Example 1, wherein the mapping guidewire includes an insulator disposed about an electrically conductive core wire.

In Example 3, the system of any of Examples 1-2, wherein each electrode comprises an exposed portion of the core wire.

In Example 4, the system of any of Examples 1-3, wherein the mapping guidewire comprises a hollow tubular member.

In Example 5, the system of any of Examples 1-4, further comprising a means for retracting the mapping guidewire within the body while measuring one or more timing intervals.

In Example 6, the system of any of Examples 1-5, further comprising a reference device configured to sense a reference electrocardiogram signal within the body.

In Example 7, the system of Example 6, wherein the analysis module is configured to determine the timing interval measurement based on the sensed electrocardiogram signal and the reference electrocardiogram signal.

In Example 8, the system of any of Examples 1-7, wherein the timing interval measurement is selected from at least one of a Q-LV interval or Q1-LV interval.

In Example 9, the system of any of Examples 1-8, wherein the user interface includes a display module and an audio module.

In Example 10, the system of Example 9, wherein the display module includes a means for visually displaying timing interval measurements on a display screen.

In Example 11 a mapping guidewire comprises an elongate body including at least one insulative member disposed about an electrically conductive member; at least one electrode configured for sensing cardiac electrical activity, the electrode comprising an exposed portion of the conductive member; and a means for electrically coupling the guidewire to a signal analyzer.

In Example 12, the mapping guidewire of Example 11, wherein the at least one electrode comprises an exposed portion of the conductive member and wherein the insulative member comprises an insulative sheath disposed about the conductive member electrically conductive member comprises a solid core wire and wherein the insulative member comprises an insulative sheath disposed about the core wire.

In Example 13, the mapping guidewire of Example 11, wherein the body includes an inner member surrounded by a first insulator and an outer member surrounded by a second insulator, and wherein the at least one electrode comprises a first electrode formed by an exposed portion of the inner member and a second electrode formed by an exposed portion of the outer member.

In Example 14, a method for selecting a cardiac lead pacing site within a body comprises inserting a first catheter into the body and cannulating a location within the body such as the coronary sinus; advancing a second catheter through the first catheter into a first branch vessel of the coronary sinus or great cardiac vein; advancing a mapping guidewire through the second catheter to a first location within the first branch vessel; sensing at least one electrical measurement at a first target pacing site within the first branch vessel; moving the mapping guidewire to one or more additional target pacing sites within the first branch vessel and sending an electrocardiogram activity signal to a signal analyzer; sensing one or more additional electrical measurements at each additional target pacing site and sending at least one additional electrocardiogram activity signal to the signal analyzer; and determining whether at least one of the target pacing sites in the first branch vessel is an optimal site.

In Example 15, the method of Example 14, wherein determining whether at least one of the target pacing sites is an optimal site includes measuring a timing interval associated with ventricular depolarization at the target pacing site and comparing the timing interval to one or more other timing intervals or a threshold timing interval.

In Example 16, the method of any of Examples 14-15, wherein determining whether at least one of the target pacing sites is an optimal site includes: sensing a reference electrical measurement within the body and sending a reference electrocardiogram signal to the signal analyzer; determining a timing interval associated with ventricular depolarization based on the sensed electrocardiogram activity signal at the target pacing site and the reference electrocardiogram signal; and comparing the timing interval to one or more other timing intervals or a threshold timing interval.

In Example 17, the method of any of Examples 14-16, wherein measuring a timing interval associated with ventricular depolarization includes measuring a first deflection of the ventricles and a ventricular polarization at the target pacing site.

In Example 18, the method of any of Examples 14-17, further comprising inserting the catheter and mapping guidewire into a second branch vessel; sensing at least one electrical measurement at one or more target pacing sites within the second branch vessel; and determining whether at least one target pacing site within the second branch vessel is an optimal site by measuring at least one timing interval.

In Example 19, the method of any of Examples 14-18, further comprising advancing a lead over the mapping guidewire and implanting the lead at a site within a vessel.

In Example 20, the method of any of Examples 14-19, further comprising providing electrical stimulus therapy to a target pacing site within a vessel using the mapping guidewire.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 7 is a perspective view showing a mapping guidewire in accordance with another illustrative embodiment;

FIG. 8 is a cross-sectional view showing the distal section of the mapping guidewire along line 8-8 in FIG. 7;

Figure 1:
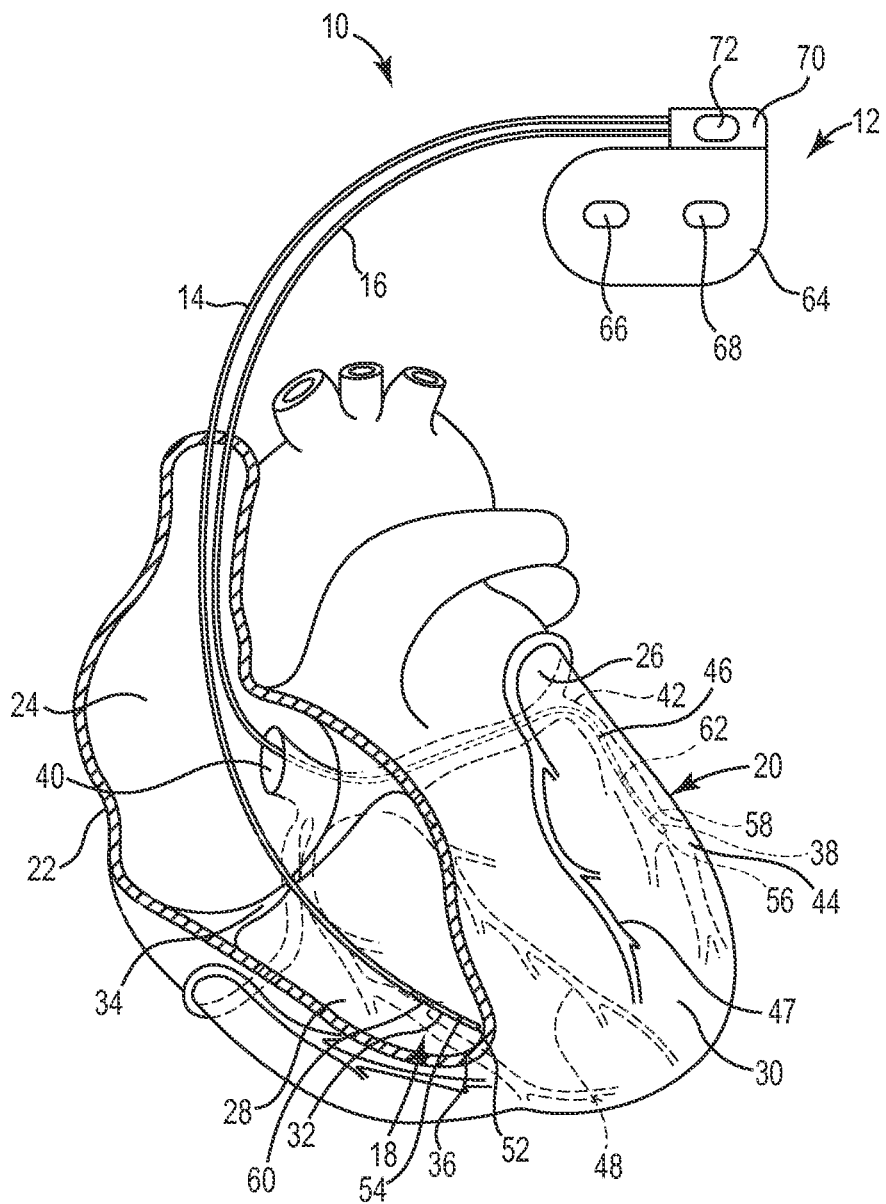
FIG. 1 is a schematic view of an implantable therapy device configured for delivering cardiac resynchronization therapy in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an implantable therapy device 10 that can be used for delivering cardiac pacing therapy in accordance with an illustrative embodiment. The therapy device 10, illustratively a CRT device for providing biventricular pacing, includes a pulse generator 12 coupled to a number of leads 14,16 that can be inserted at target implantation pacing sites 18,20 in or near a patient's heart 22. The heart 22 includes a right atrium 24, a left atrium 26, a right ventricle 28, and a left ventricle 30. As shown in FIG. 1, the distal portion 32 of a first, right ventricular (RV) lead 14 may be transvenously guided through the right atrium 24, through the tricuspid valve 34, and into the apex 36 of the right ventricle 28. The distal portion 38 of a second, left ventricular (LV) lead 16, in turn, may be tranvenously guided through the right atrium 24, through the coronary sinus ostium 40, and into a branch vessel of the coronary sinus 42, great cardiac vein 44, or other cardiac vessel located adjacent to the left side of the heart 22. In some embodiments, for example, the distal portion 38 of the LV lead 16 may be implanted in a lateral coronary vein 46, as shown. Alternatively, and in other embodiments, the distal portion 38 of the LV lead 16 may be implanted in another coronary vessel such as an anterior vein 47 or posterior vein 48.

Each of the leads 14,16 can include one or more cardiac pace/sense electrodes for sensing electrical measurements within the patient's heart 22 and for delivering pacing pulses and/or defibrillation energy to the heart 22. In some embodiments, for example, the RV lead 14 includes a number of pacing electrodes 52, 54 for sensing electrical activity within the right ventricle 28 of the heart 22 and/or to provide pacing pulses to the right ventricle 28. The LV lead 16 positioned in a cardiac vein adjacent to the left side of the heart 22, in turn, includes a number pacing electrodes 56, 58 for sensing electrical activity within the heart 22 and/or to provide pacing pulses to the left ventricle 30. In some embodiments, a number of defibrillation electrode coils 60, 62 provided on one or both of the leads 14,16 can be utilized to deliver defibrillation/ cardioversion shocks to the patient's heart 22, if necessary.

Cardiac rhythm management (CRM) circuitry within the pulse generator 12 provides electrical stimulation pulses to the lead electrodes 52, 54, 56, 58 and, in some cases, defibrillation energy to the cardioversion/defibrillation electrodes 60, 62. In some embodiments, the CRM circuitry is configured for selecting pacing electrode(s), electrode sites, timing/delay sequences and/or pacing output configurations to be applied via the lead electrodes 52, 54, 56, 58. In some embodiments, the CRM circuitry includes functionality to diagnose a change in a patient's hemodynamic status based on one or more timing interval measurements derived from electrical signals sensed from one or more of the lead electrodes 52, 54, 56, 58, or from physiologic signals derived from one or more hemodynamic sensors such as a pressure sensor. In certain embodiments, the CRM circuitry includes functionality for detecting and treating cardiac tachyarrhythmia using defibrillation therapy and/or anti-tachyarrhythmia pacing (ATP) pacing. Embodiments providing defibrillation therapy may utilize the defibrillation electrodes 60, 62 for delivering high energy shocks to the heart 22 to terminate or mitigate tachyarrhythmia.

Communication circuitry within the pulse generator 12 facilitates communication between the therapy device 10 and a patient external device such as an external programmer or advanced patient management (APM) system. The communication circuitry may also facilitate communication with one or more implanted, external, cutaneous, or subcutaneous physiologic or non-physiologic sensors, patient-input devices and/or information systems. In some embodiments, and as discussed further below, the communication circuitry may also facilitate communication between the pulse generator 12 and a signal analyzer 78 (FIG. 2) that can be used by the clinician in implanting the leads 14, 16 at target sites within the body responsive to a pacing therapy protocol such as CRT. In some embodiments, for example, the communication circuitry includes wireless communication circuitry that allows the pulse generator 12 to communicate with one or more other devices using electromagnetic, RF, inductive, or acoustic telemetry.

In some embodiments, portions of the pulse generator housing 64 include can electrodes 66, 68, which serve as reference electrodes for one or both of the leads 14,16. A header 70 on the housing 64 serves to connect the leads 14, 16 to the CRM circuitry, and in some embodiments further includes one or more indifferent electrodes 72. The pulse generator 12 can include one or more additional electrodes and/or sensors for sensing various physiological parameters. During therapy delivery, the CRM circuitry controls the cardiac electrodes 52, 54, 56, 58 and other sensors/electrodes 66, 68, 72 disposed on or within the pulse generator 12 to produce signals used for detecting and/or measuring various physiological parameters. Example parameters that can be detected and/or measured include, but are not limited to, transthoracic impedance, respiratory rate, minute ventilation, heart rate, heart rate variability, cardiac dysynchrony, activity, posture, blood chemistry, O2 saturation, heart sounds, wall stress, strain, hypertrophy, inter-electrode impedance, electrical timing delays (e.g., PR interval, AV interval, QRS width, etc.), cardiac chamber pressure (e.g., RV and/or LV ventricular pressure), vascular pressure (e.g., pulmonary artery pressure), cardiac output, temperature, depolarization amplitudes, and depolarization timing. Information from one or more of these physiological parameters may be used to adjust operating parameters such as the amplitude, timing, and/or pulse width of the stimulus energy delivered to the leads 14, 16 from the pulse generator 12.

In certain embodiments, the pulse generator 12 may transfer sensed or derived information relevant to pacing output configuration or diagnosis to a patient-external device. In such case, selection of a pacing output configuration and/or diagnosis of hemodynamic status may be made by the patient-external device or by a clinician using information provided by the patient-external device. Alternatively, or in addition, the therapy device 10 itself may determine the pacing output configuration and/or diagnose the hemodynamic status of the patient.

Pacing output configuration involves the selection of the site or sites for cardiac pacing and/or the temporal sequence of pacing pulses delivered to each of multiple pacing sites. In some embodiments, the pacing output configuration can further include the selection of particular pulse characteristics (e.g., amplitude, duration, anodal/cathodal polarity, AV interval, and wave shape) used for the pacing pulses. Selection of the pacing output configuration is particularly useful for cardiac resynchronization therapy applications. In particular, the location of pacing site or sites and/or other properties of the pacing output configuration affects the spread of depolarization excitation, which in part determines the manner in which the heart chambers contract. In a therapy device equipped with multiple electrodes disposed at multiple pacing sites in or near the heart, the ability to select between one or more electrodes, to adjust the temporal pacing sequence, and/or to adjust the pulse waveform characteristics of the pacing pulses can be used to increase contractility function of the heart.

For some CRT applications, the selection of a target pacing site for implanting each of the leads may depend in part on the cardiac electrode placement and/or the pacing output configuration. Not all possible cardiac electrode sites are ideal for effective cardiac pacing. For example, some cardiac electrode sites for pacing a particular patient's left ventricle may not significantly improve overall cardiac output when paced due to the nature of the patient's heart condition. As discussed further herein, an electrode site that when compared to other potential electrode sites provides a relative improvement in overall cardiac output can be considered to be an optimal or optimized site for lead implantation.

Prior to cardiac electrode placement or pacing output configuration, it is often helpful to determine which target site or sites may be optimal sites that improve cardiac output when paced. Balanced against this selection of sites are other factors the clinician must normally consider during the implantation process such as the size of the vessel and the ease of inserting the lead into the vessel. Other considerations such as the pacing thresholds and the potential risk of phrenic nerve stimulation may also be considered in the selection of a target site.

Figure 2:
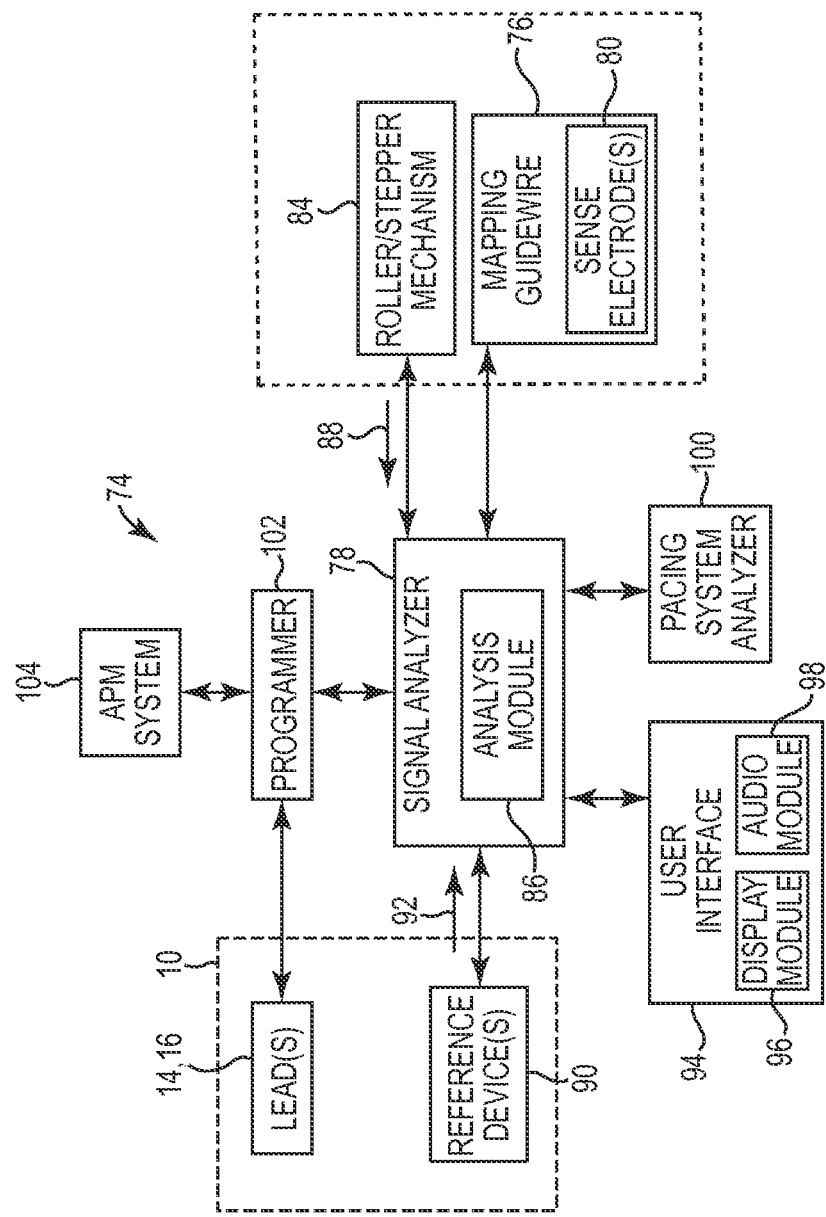
FIG. 2 is a block diagram showing a cardiac lead implantation system in accordance with an illustrative embodiment.

FIG. 2 is a block diagram showing a cardiac lead implantation system 74 in accordance with an illustrative embodiment. The system 74, illustratively a lead implantation system for aiding and/or optimizing the placement of a CRT lead for use in providing cardiac resynchronization therapy, includes a therapy device 10, a mapping guidewire 76 for aiding in the placement and implantation of the therapy device leads 14, 16, and a signal analyzer 78 for use by the clinician in determining whether a selected target site or sites within a patient are optimal sites. For purposes of illustration and not limitation, the system 74 may be used to aid in the implantation of an LV lead 16 for a biventricular pacing system such as that described above with respect to FIG. 1. Alternatively, and in other embodiments, the system 74 may be used to aid in the implantation of other leads on or within the heart. For example, the system 74 may be used to implant leads in the right atrium, the right ventricle, the left atrium, the left ventricle, and/or in other cardiac vessels that lead into or from the heart. In some embodiments, the system 74 may be used to facilitate epicardial or endocardial pacing site optimization.

The mapping guidewire 76 includes one or more sense electrodes 80 that can be used to sense cardiac electrical activity within the body. During the implantation procedure, the sense electrodes 80 are configured to sense electrical activity at multiple, fiducial points along a pathway within the body which, as discussed herein, can be used to map electrical delays within the heart. In some embodiments, the guidewire 76 includes multiple electrodes 80, and is configured to operate in a bipolar mode for sensing cardiac electrical activity. Alternatively, and in other embodiments, the guidewire 76 includes one or more electrodes 80 that each operate in a unipolar mode for sensing cardiac electrical activity. When operating in a unipolar mode, in some embodiments, a reference electrode (e.g., a can electrode 66, 68 or indifferent electrode 72) coupled to the pulse generator 12 may be used as a return electrode (e.g., an anode) for each of the electrodes 80 on the guidewire 76.

In some embodiments, a roller/stepper mechanism 84 coupled to the mapping guidewire 76 can be used by the signal analyzer 78 to control the retraction of the mapping guidewire 76 within the body as electrical timing delay values are measured. In some embodiments, for example, the roller/stepper mechanism 84 comprises a servo mechanism that can be controlled by the signal analyzer 78 to retract the guidewire 76 in a continuous manner for mapping electrical delays at specific locations within the body. In certain embodiments, feedback provided by the roller/stepper mechanism 84 as to the precise location of a site within the body can be provided to the signal analyzer 78 which, in turn, can be used to gauge later implantation of the lead to that exact site, and which provides a precise electrical delay map within the vein.

An analysis module 86 within the signal analyzer 78 receives the ECG activity signals 88 sensed by the mapping guidewire 76 (and as discussed further below in some cases also a reference ECG signal 92), and based on these signals, calculates a timing interval parameter. In some embodiments, the analysis module 86 may identify and prioritize potential stimulation target sites based on various timing interval measurements associated with ventricular depolarization as derived from a number of different candidate sites using the mapping guidewire 76 and reference ECG signal 92. The timing parameter value can be displayed and/or compared to other parameter values to determine the optimal pacing site for implanting the lead. The timing parameter value can also be stored in memory for later review and/or for registering with a venogram to generate an electrical delay map of venous anatomy. In certain embodiments, the mapping guidewire 76 may also be used to determine the patient's hemodynamic status or to detect a change in hemodynamic status.

An optimized site can be characterized by late activation of depolarization and/or prolonged depolarization. For the implantation of leads configured for stimulating the left ventricle in a biventricular pacing system such as that described above with respect to FIG. 1, for example, the sites can be assessed by the signal analyzer 78 through an analysis of a timing interval (e.g., Q1-LV or Q-LV) defined between a first deflection (e.g., Q1 or Q) and a maximum deflection (e.g., LV) of a ventricular polarization for a given electrode site. The Q1-LV interval refers to a timing interval defined between the start of a QRS deflection of a sensed LV electrogram and the peak of the QRS deflection of the LV electrogram. The Q-LV timing interval, in turn, refers to a timing interval defined between the start of a QRS deflection of a surface electrogram and the peak of the QRS deflection of the LV electrogram. An example of selecting a pacing output configuration for CRT applications based on sensing various timing interval measurements is discussed further in U.S. Pat. No. 7,890,172, which is incorporated herein by reference in its entirety for all purposes.

In certain embodiments, another connection port on the signal analyzer 78 can be coupled to a second, reference device 90 such as a surface EKG electrode or another implanted lead electrode (e.g., an RV lead electrode 14) for providing a reference electrocardiogram signal 92 for calculating timing intervals associated with proposed cardiac electrode sites. The reference device 90 may comprise, for example, an implantable RV lead used to sense electrical activity within the right ventricle, an RA lead used to sense electrical activity in the right atrium, or a surface EKG electrode placed on the patient's chest or limb.

The analysis module 86 can be configured to assess CRT responsiveness for each of a number of target pacing electrode sites. For example, the analysis module 86 in conjunction with sensed electrocardiogram activity signals 88 from the mapping guidewire 76, and in some embodiments also the reference electrocardiogram signals 92 from the reference device 90, may assess a parameter associated with a degree of responsiveness of a left ventricular electrode site to cardiac resynchronization. Such parameters may include depolarization characteristics such as depolarization delays (e.g., Q1-LV or Q-LV interval), atrioventricular intervals, depolarization amplitude, depolarization-repolarization intervals, depolarization threshold, and/or other depolarization characteristics. In some embodiments, the analysis module is configured to identify features of a sensed signal corresponding to an atrial and/or ventricular depolarization/repolarization. Such features may include, for example, the start of a ventricular depolarization, a peak initial deflection corresponding to a ventricular depolarization, and/or a maximum deflection associated with ventricular depolarization.

The signal analyzer 78 further includes an interface 94 to facilitate adjusting various settings within the analyzer 78, and to provide the clinician with feedback on one or more sites under evaluation. The interface 94 includes a display module 96 such as a monitor or display panel for displaying various sensed and/or computed values. For example, the display module 96 can be configured to display the timing interval associated with a target site currently under consideration as a potential site, one or more previous timing intervals stored by the signal analyzer 78, the pacing threshold associated with a selected target site, sensed electrocardiogram waveforms or corresponding waveform values received from the mapping guidewire 76, sensed electrocardiogram waveforms or corresponding values received from each reference device 90, as well as other information. Other visual information can also be provided to the clinician via the interface 94. For example, the signal analyzer 78 can include a number of LED lights or a colormap on a display screen indicating in a first color (e.g., green) that the timing interval is at or above a predefined timing threshold (e.g., 80 ms) indicating that the site is an optimal site and another color (e.g., red) indicating that the timing interval is below the threshold (e.g., <80 ms), indicating that the site is not an optimal site.

Other information can also be provided to the clinician via the interface 94 to aid the clinician in implant site decision making. In some embodiments, for example, the signal analyzer 78 further includes an audio module 98 such as a speaker or buzzer that provides the clinician with aural feedback on a target pacing site. In one such embodiment, for example, the audio module 98 can be configured to output a continuous tone that increases in intensity or frequency as the mapping guidewire 76 is advanced from one site to another site. As another example, the intensity or frequency of a continuous tone may increase or decrease as the electrical impedance of the mapping guidewire's electrode(s) increases or decreases. Other user perceivable audio variations can include changes of tone, tone burses with varying tone pulse widths, pulse repetition rates, and combinations of these audible characteristics. In one embodiment, an audible signal can be emitted the intensity or frequency of which is proportional to the timing interval (e.g., Q-LV) measured by the mapping guidewire 76 at a target pacing site.

In some embodiments, the signal analyzer 78 is integrated with a pacing system analyzer (PSA) 100 that can be used by the clinician to further test lead impedance of an implanted lead 14, 16 and/or to sense pacing amplitude thresholds before connecting the lead 14, 16 to the pulse generator 12. Alternatively, and in other embodiments, the signal analyzer 78 may comprise a device separate from the PSA 100. In some embodiments, the signal analyzer 78 can be integrated with a programming device 102 and/or an advanced patient management (APM) system 104 used for programming the pulse generator 12.

Figure 3:
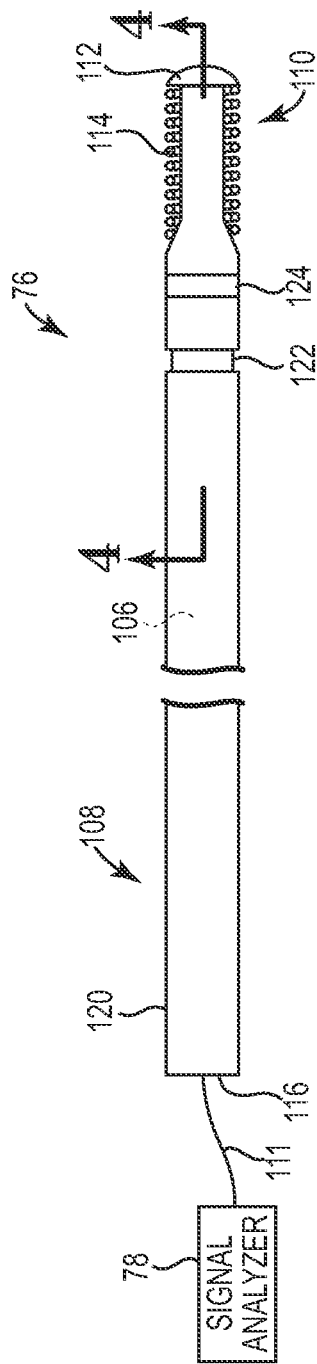
FIG. 3 is a perspective view showing an illustrative mapping guidewire for use in determining potential lead implantation sites within a body.

FIG. 3 is a perspective view showing an illustrative mapping guidewire 76 for use in determining potential sites within a body for cardiac lead implantation. In the embodiment shown, the guidewire 76 comprises a solid core wire 106 extending from a proximal section 108 to a distal section 110 of the guidewire 76. The proximal section 108 of the guidewire 76 can be manipulated by a clinician from a position outside of the body manually, with the aid of a roller/stepper mechanism 84, and/or by other suitable means. The distal section 110 of the guidewire 76, in turn, includes a flexible distal tip 112 to facilitate traversal of the guidewire 76 through the body to one or more target pacing sites. A flexible coil 114 disposed adjacent to a reduced-diameter portion of the core wire 106 imparts added flexibility to the guidewire 76.

The solid core wire 106 is made from an electrically conductive material, and is coupled at a proximal end 116 of the guidewire 76 to the signal analyzer 78 via an electrical connector 111. An insulative sheath 120 comprising polytetrafluoroethylene (PTFE) or other suitable non-conductive material is disposed about the outer surface of the core wire 106, and serves to electrically insulate the core wire 106 from the surrounding body tissue along the length of the guidewire 76.

The outer diameter of the guidewire 76 can vary depending on the size and anatomy to be traversed by the guidewire 76, the size of other instruments used in advancing the guidewire 76 to target site(s) within the body, as well as other factors. In some embodiments, the guidewire 76 may also serve to later guide the lead into position at the selected pacing site subsequent to mapping potential target sites within the body. In some embodiments, the outer diameter of the guidewire 76 may also be dimensioned to fit within a guidewire or stylet lumen of the lead to be implanted, permitting the lead to be advanced to the implantation site using an over-the-wire approach over the guidewire 76. The outer diameter of the guidewire 76 may vary from between about 0.010 inches to about 0.050 inches, although other dimensions greater and smaller than these values are contemplated. In some embodiments, the guidewire 76 can include a 0.014 inch version and a 0.038 inch version, which correspond to that of guidewires used in many cardiac lead implantation systems.

In use, the solid core wire 106 serves as an electrical conductor for transmitting electrocardiogram signals sensed by the guidewire 76 to the signal analyzer 78 for analysis. In some embodiments, an exposed portion 122 of the core wire 106 located on the distal section 110 of the guidewire 76 forms an electrode that can be used by the signal analyzer 78 to detect and monitor cardiac electrical activity. In some embodiments, the exposed portion 122 or another portion of the guidewire 76 can be used for pacing the heart to determine the pacing amplitude threshold at a potential site. A radiopaque marker 124 located on the distal section 110 of the guidewire 76 can be used to facilitate guidewire delivery and to gauge the location of the electrode 122 within the body.

In a unipolar configuration, a reference electrode on another implanted lead, pulse generator, catheter, or other reference device may serve as an anode for each guidewire electrode 122. In another embodiment, the guidewire 76 includes a hollow core construction with a second, internal electrical conductor to permit bipolar sensing of cardiac electrical activity within the body, or a small cable extending along the outside of the guidewire under the polymer sleeve. In one embodiment, for example, the distal tip 112 may be formed from an electrically conductive material, and is electrically coupled to one terminal on the signal analyzer 78. Other unipolar and bipolar guidewire electrode configurations are also possible. In one embodiment, for example, a first exposed portion on the guidewire 76 may function as a first electrode (e.g., a cathode) and a second exposed portion on the guidewire 76 can be used as a second electrode (e.g., an anode).

In some embodiments, the guidewire electrode 122 can also be used as a pacing electrode to permit the clinician to test whether a particular target pacing site is responsive to electrical pacing pulses at that location. For example, the electrode 122 can be used in some embodiments as confirmation that a proposed site is responsive to electrical stimulus and does not result in phrenic nerve stimulation and/or that the site is likely to result in adequate capture and activation by the lead once implanted.

Figure 4:
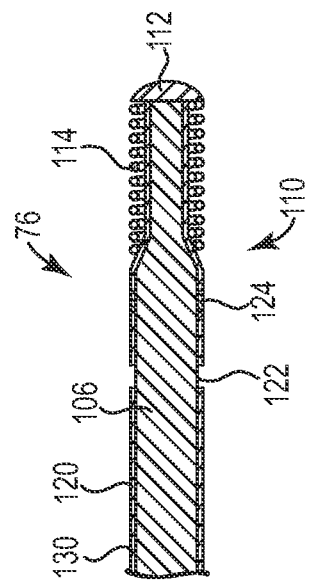
FIG. 4 is a cross-sectional view showing the mapping guidewire along line 4-4 in FIG. 3.

FIG. 4 is a cross-sectional view showing the mapping guidewire 76 along line 4-4 in FIG. 3. As can be further seen in FIG. 4, and in some embodiments, the exposed electrode portion 122 comprises a portion of the guidewire 76 in which the insulative sheath 120 has been removed to expose the outer surface 130 of the core wire 106. In the embodiment shown in FIG. 4, the insulative sheath 120 is removed about the entire circumference of the guidewire 76, forming a ring-shaped electrode surface 122. In other embodiments, only a portion of the insulative sheath 120 is removed circumferentially about the guidewire 76, forming a semi-ring shaped electrode surface. Other configurations are also contemplated.

In some embodiments, the proximal section 108 of the guidewire 76 can be configured similar to the distal section 110, including a number of sections with the insulative sheath 120 removed to expose the core wire 106. In those embodiments in which the core wire 106 is hollow and a conductor runs through the guidewire 76, a separate ring similar to that formed by the exposed portion 122 may be used to electrically couple the guidewire 76 to the signal analyzer 78. In some embodiments, for example, alligator clips may be attached to an exposed portion on the proximal section 108 to connect the signal analyzer 78 to the guidewire 76.

Figure 5:
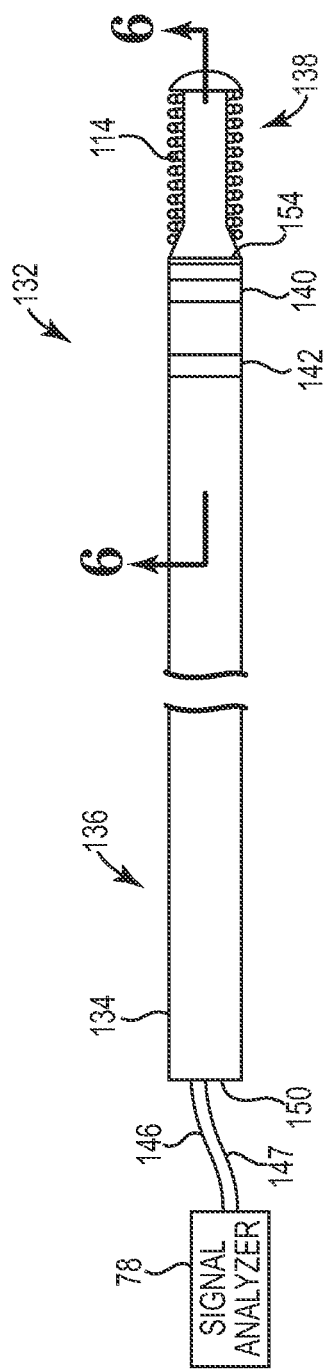
FIG. 5 is a perspective view showing a mapping guidewire in accordance with another illustrative embodiment.

FIG. 5 is a perspective view showing a mapping guidewire 132 in accordance with another illustrative embodiment. In the embodiment of FIG. 5, the guidewire 132 comprises a hollow tubular member housing 134 having a proximal section 136 and a distal section 138. The proximal section 136 can be manipulated by a clinician from a position outside of the body manually, with the aid of a roller/stepper mechanism 84, and/or by other suitable means. The distal section 138 of the guidewire 132, in turn, is configured to facilitate traversal to one or more target pacing sites.

In the embodiment of FIG. 5, the distal section 138 of the tubular member housing 134 includes one or more electrodes 140, 142 configured for sensing cardiac electrical activity within the body. The electrodes 140, 142 are made from an electrically conductive material, and are electrically coupled to the signal analyzer 78 via a number of electrical conductors which extend from the distal section 138 to a proximal end 150 of the tubular member housing 134. A radiopaque marker 154 located on the distal section 138 of the guidewire 132 can be used to facilitate guidewire delivery and to gauge the location of the electrodes 140, 142 within the body.

Figure 6:
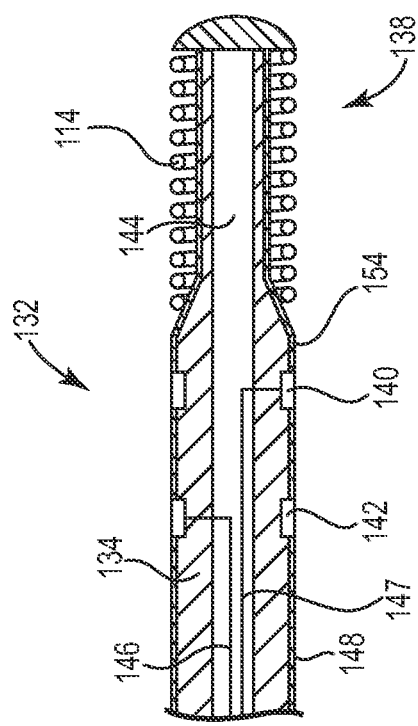
FIG. 6 is a cross-sectional view showing the distal section of the mapping guidewire along line 6-6 in FIG. 5.

FIG. 6 is a cross-sectional view showing the distal section of the mapping guidewire 132 along line 6-6 in FIG. 5. As can be further seen in FIG. 6, and in some embodiments, the tubular member housing 134 includes an internal lumen 144 which contains a wire conductor 146 connected to one of the electrodes (e.g., the proximal electrode 142) and to the signal analyzer 78. The housing 134, in turn, can be formed from an electrically conductive material, and is electrically coupled to another electrode (e.g., the distal electrode 140) and to the signal analyzer 78 via a conductor 147. A layer of insulation 148 disposed about the housing 134 electrically insulates the guidewire 132 from the surrounding body tissue. A portion of the insulation 148 is exposed at the location of each of the electrodes 140, 142.

In use, the electrodes 140, 142 are configured to sense cardiac electrical activity within the body and transmit electrocardiogram activity signals 88 to the signal analyzer 78 for analysis. In some embodiments, each of the electrodes 140, 142 operate in a bipolar mode. Alternatively, and in other embodiments, each of the electrodes 140, 142 may operate in a unipolar mode, and a reference electrode on another implanted lead, pulse generator, catheter, or other reference device serves as an anode for the electrodes 140, 142. In some embodiments, a radiopaque marker band 154 may be used by the clinician to facilitate guidewire delivery and/or to gauge the location of the electrodes 140, 142 within the body.

FIG. 7 is a perspective view showing a mapping guidewire 212 in accordance with another illustrative embodiment. In the embodiment of FIG. 7, the guidewire 212 comprises a hollow tubular member housing 214 having a proximal section 216 and a distal section 218. The proximal section 216 can be manipulated by a clinician from a position outside of the body manually, with the aid of a roller/stepper mechanism 84, and/or by other suitable means. The distal section 218 of the guidewire 212, in turn, is configured to facilitate traversal to one or more target pacing sites.

In the embodiment of FIG. 7, the distal section 218 of the tubular member housing 214 includes a pair of electrodes 222, 223 configured for sensing cardiac electrical activity within the body. A similar set of electrodes 220, 221 on the proximal section 216 of the tubular member housing 214 are provided for electrically connecting the mapping guidewire 212 to the signal analyzer 78. A radiopaque marker 226 located on the distal end 228 of the guidewire 212 can be used to facilitate guidewire delivery and to gauge the location of the distal pair of electrodes 222 and 223 within the body.

FIG. 8 is a cross-sectional view showing the distal section 218 of the mapping guidewire 212 along line 8-8 in FIG. 7. As can be further seen in FIG. 8, and in some embodiments, the tubular housing 214 includes an inner core member 230 surrounded at least in part by an outer member 232. The inner core member 230 comprises an electrically conductive material, and is surrounded by a non-conductive insulator 234. The outer member 232 also comprises an electrically conductive material, and is surrounded by a non-conductive insulator 236. A portion 238 of the insulator 234 surrounding the core member 230 is exposed, forming a first electrode 223 along the housing 214. A portion 240 of the insulator 236 surrounding the outer member 232 is also exposed, forming a second electrode 222 along the housing 214.

In use, the electrodes 222 and 223 are configured to sense cardiac electrical activity within the body and transmit electrocardiogram activity signals to the signal analyzer for analysis. In some embodiments, each of the electrodes 222 and 223 operate in a bipolar mode. Alternatively, and in other embodiments, each of the electrodes 222 and 223 may operate in a unipolar mode, and a reference electrode on another implanted lead, pulse generator, catheter, or other reference device serves as an anode for the electrodes 222 and 223.

Figure 9A:
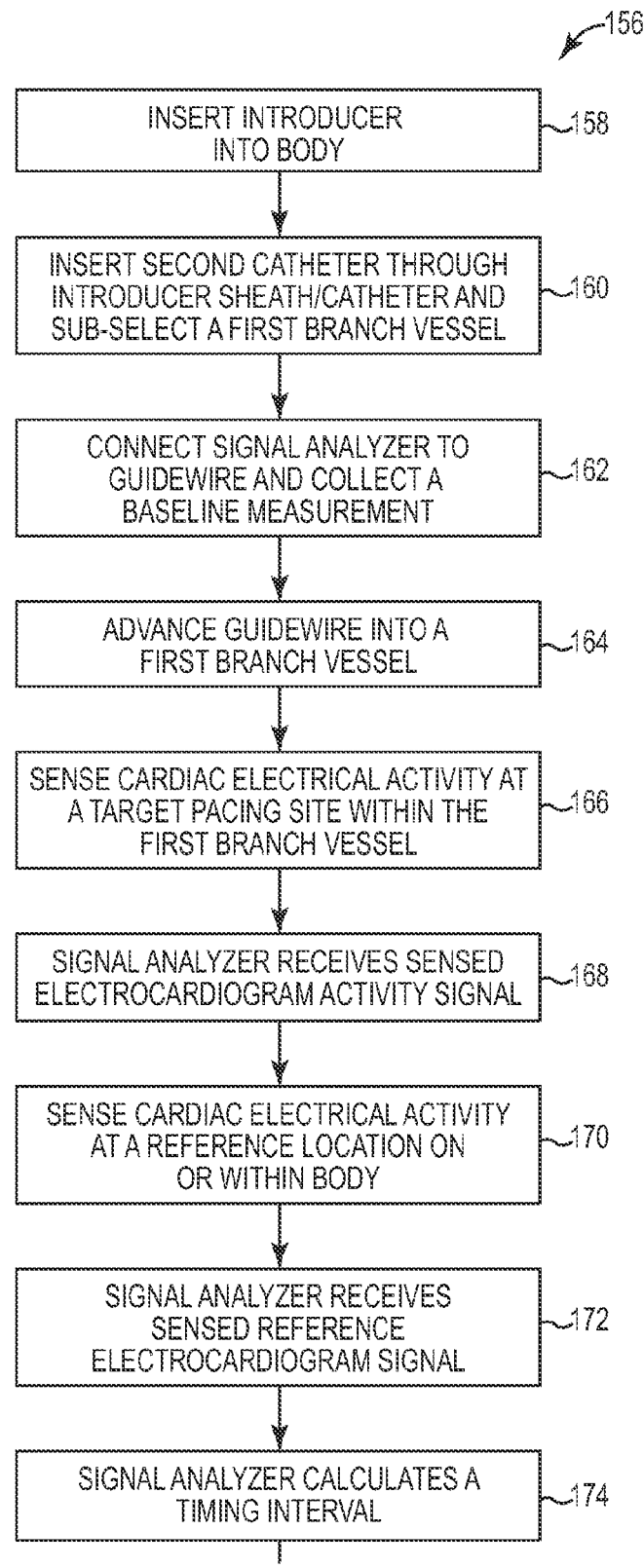
FIGS. 9A-9B are a flow diagram showing an illustrative method for selecting a lead pacing site in accordance with an illustrative embodiment.
Figure 9B:
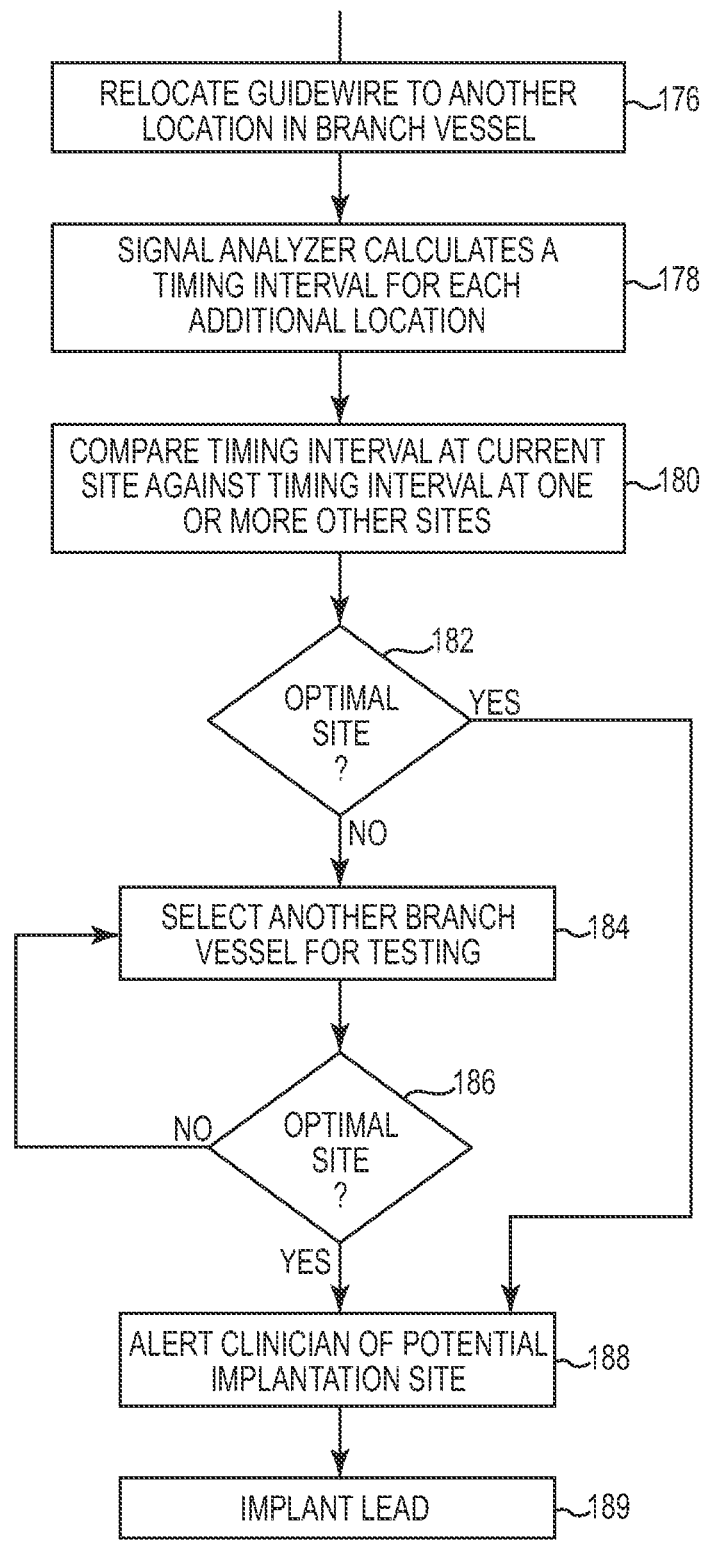

FIGS. 9A-9B are a flow diagram showing an illustrative method 156 for selecting a lead pacing site in accordance with an illustrative embodiment. In some embodiments, the method 156 may comprise several steps that can be used for selecting one or more optimal sites for implanting a CRT lead 14, 16 using the cardiac lead implantation system 74 of FIG. 2. In other embodiments, the method 156 may be used to implant other types of cardiac therapy devices and/or leads in other locations within the body such as endocardial leads or epicardial leads. The method 156 can also be used for implanting other, non-cardiac leads such as neurostimulation pacing leads.

The method 156 may begin generally at steps 158 and 160 in which an introducer is used for percutaneous access to a blood vessel, and then a catheter (e.g., a guide catheter) is used to cannulate a particular location within the body, allowing the mapping guidewire 76, 132, 212 and/or other devices to be later inserted into the body for advancement to one or more target pacing sites. In some embodiments, for example, a telescoping introducer catheter is inserted into the body at a percutaneous access site (e.g., a jugular vein or femoral artery), and is advanced to a location within the body to permit a second instrument (e.g., a guide catheter or guidewire) to cannulate a vessel or chamber. In the implantation of a cardiac lead 14 to be implanted into a cardiac vein for providing CRT therapy to a left ventricle or left atrium of a heart, for example, an introducer may be inserted percutaneously into the body and advanced to the right atrium. A catheter may be used to cannulate a location within the body such as the coronary sinus ostium. This cannulation provides a pathway for a second, inner catheter, the mapping guidewire 76, 132, 212 and/or one or more other instruments to be inserted into the coronary sinus and into a branch of the coronary sinus, great cardiac vein, or other cardiac branch vessel located adjacent to the left side of the heart.

Upon cannulation, a second, inner catheter may be inserted through the catheter to sub-select a first branch vessel (block 160) within the body. In some embodiments, for example, a second catheter configured for insertion through the interior lumen of the catheter may be advanced to a second location within the body within a branch vessel of the coronary sinus such as a posterior branch cardiac vein or middle lateral branch cardiac vein. Once the vein is sub-selected, the mapping guidewire 76, 132, 212 is inserted through the inner catheter to a location within the branch vein. The signal analyzer 78 is connected to the mapping guidewire 76, 132, 212 and a baseline measurement is collected (block 162). In some embodiments, for example, an impedance test is performed on the guidewire 76, 132, 212 to confirm proper electrical connection of the guidewire to the signal analyzer 78. The mapping guidewire 76, 132, 212 is then advanced through the second catheter to a target pacing site within the first branch vessel (block 164).

Once positioned within the first branch vessel, the signal analyzer 78 may then utilize one or more of the guidewire electrodes for sensing cardiac electrical activity at the target site (block 166). The electrocardiogram activity signals 88 sensed by the mapping guidewire 76, 132, 212 are fed to the signal analyzer 78 (block 168). In some embodiments, a reference device 90 such as another implanted lead or a surface EKG also senses cardiac electrical activity at a different location within the body such as in the right atrium or right ventricle (block 170), and provides the signal analyzer 78 with a reference electrocardiogram signal 92 (block 172).

The analysis module 86 compares the electrical activity signal 88 and in some cases also the reference signal 92, and from these signals 88, 92 calculates a timing interval that can later be used to determine whether a particular site is an optimal site for lead implantation (block 174). In some embodiments, the analysis module 86 calculates a timing interval associated with ventricular depolarization by measuring a first deflection (e.g., Q1 or Q) and a maximum deflection (e.g., LV) of a ventricular polarization. Examples of other timing intervals that can be measured include RV-LV, RA-LV, Q*-LV, etc.

Once one or more electrocardiogram measurements are taken at the target pacing site, the clinician next retracts the mapping guidewire 76, 132, 212 within the branch vessel, relocating the guidewire 76, 132, 212 to another location within the branch vessel closer to the origin of the vessel (block 176). As the guidewire 76, 132, 212 is retracted, the signal analyzer 78 can be configured to calculate a timing interval for each additional target site (block 178).

The signal analyzer 78 can be configured to compare the timing interval (e.g., Q-LV) measured at the current target pacing site against the timing interval measured at one or more previous target sites to determine whether the current site is an optimal site for lead implantation (block 180). Other timing intervals can also be used to determine whether a particular site is an optimal site. Other parameters in addition, or in lieu of timing intervals can also be used to determine whether the current pacing site is optimal. In certain embodiments, for example, the guidewire 76, 132, 212 can be used to sense the pacing amplitude threshold at a particular site, which can then be compared to the amplitude threshold sensed at other locations and/or a pre-determined threshold value to determine if the current site is optimal. Other characteristics such as the likelihood of phrenic nerve stimulation can also be used to determine whether the current site is optimal.

In some embodiments, the sensed timing intervals can be compared against a threshold value in order to determine whether a candidate pacing site is optimal. The threshold values used for comparison will typically vary depending on the particular timing interval sensed. For Q-LV or Q1-LV timing intervals, for example, the threshold value for determining whether the site is optimal may be set at or above 80 ms. Conversely, for far field sensing using Q*-LV timing intervals, a higher threshold (e.g., 100 ms) may be used to determine whether a particular site is an optimal site. The particular threshold criteria for a given timing interval will typically vary depending on the ventricular depolarization characteristics of the patient, and will thus vary from patient to patient.

If during the process of testing target pacing sites for each branch vessel the signal analyzer 78 detects that one of the target pacing sites is an optimal site (block 182), the signal analyzer 78 alerts the clinician of the presence of the potential implantation site (e.g., via the user interface 94), prompting the clinician to consider that site as a possible implantation site for the lead electrode (block 188). In certain embodiments, for example, the signal analyzer 78 may alert the clinician that the current site is an optimal site if the timing interval at the current site is greater than that measured at one or more previous target sites. In other embodiments, the signal analyzer 78 may alert the clinician that the current site is an optimal site if the timing interval is greater than that measured at one or more previous target sites and the current timing interval exceeds a threshold timing interval value.

If the clinician determines at decision block 182 that none of the target pacing sites are optimal, or if the clinician desires to consider other branch vessels for insertion of the lead, the clinician may then withdraw the mapping guidewire 76, 132, 212 back into the catheter and select another branch vessel for testing (block 184). If, for example, the first branch vessel tested is a posterior branch cardiac vein, and the signal analyzer 78 determines that no target pacing sites were optimal, then the clinician may retract the mapping guidewire 76, 132, 212 back into the catheter and advance the catheter/guidewire to a more lateral branch vessel for testing (block 186) in a manner similar to that performed for the first branch vessel. The process may then be repeated one or more times for additional branch vessels to be analyzed.

The clinician may then implant the lead at the site (block 189) or continue the process of selecting other branch vessels for considering other potential pacing sites. Once a site has been selected, the lead may then be advanced over the guidewire 76, 132, 212 to the site. The implanted lead may then be secured within the vessel and tested using a PSA 100 and/or programmer 102 to confirm that the selected site results in activation. If desired, the method 156 may then be repeated for determining other suitable sites for implanting other leads within the body. Other additional steps may also be performed to program the therapy device 10, including the selection of pacing output configuration based on the timing intervals associated with the selected implantation site.

FIGS. 10-15 are several views showing a number of example steps used for selecting a lead pacing site within a branch coronary vein using the lead implantation system 74 of FIG. 2. FIGS. 10-15 may represent, for example, several illustrative steps that can be used for selecting a lead pacing site using the method 156 described herein with respect to FIGS. 9A-9B. The selection of target regions within the body may differ from that shown, however, depending on the particular application.

Figure 10:
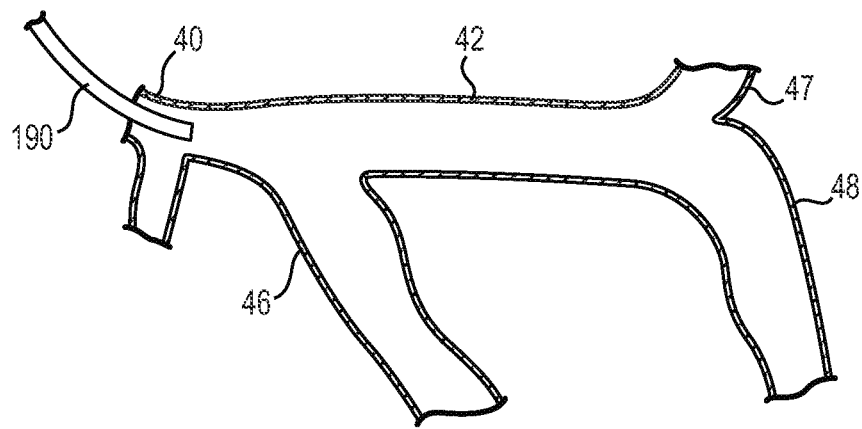
FIGS. 10-15 are several views showing a number of illustrative steps used for selecting a lead pacing site using the lead implantation system of FIG. 2.

In a first step depicted in FIG. 10, a catheter 190 is inserted into the coronary sinus ostium 40 for cannulating the coronary sinus 42. Once cannulated, and as further shown in a second step in FIG. 11, a second catheter 192 can be inserted into the catheter 190 and advanced beyond the distal end 194 of the catheter 190 to a first branch vessel within the body such as a posterior branch coronary vein 196, as shown. The particular branch vessel selected may differ, however, depending on the size of the vessel, the ease of inserting the catheter 192 into the branch vein, as well as other factors. An interior lumen 198 within the second catheter 192 can be configured to carry a mapping guidewire (e.g., guidewire 76) which as shown in FIG. 11, can be advanced distally beyond the distal end 200 of the catheter 192 once the catheter 192 is positioned within the branch vessel 196.

Figure 11:
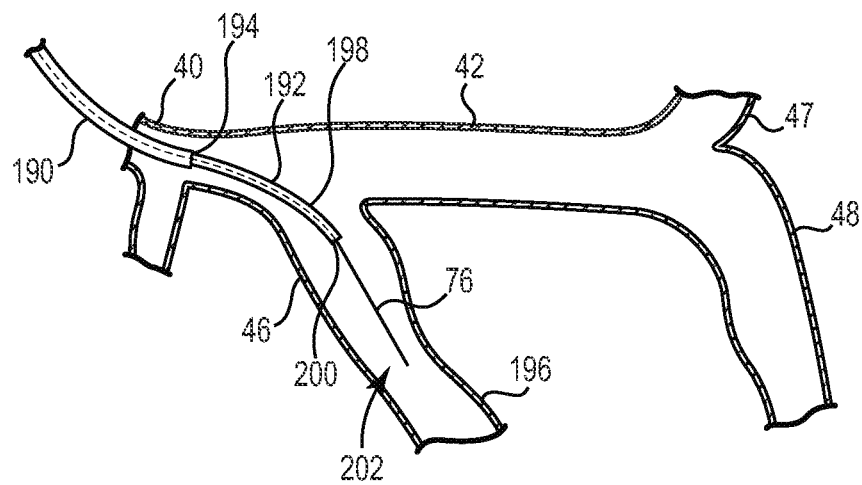
Figure 12:
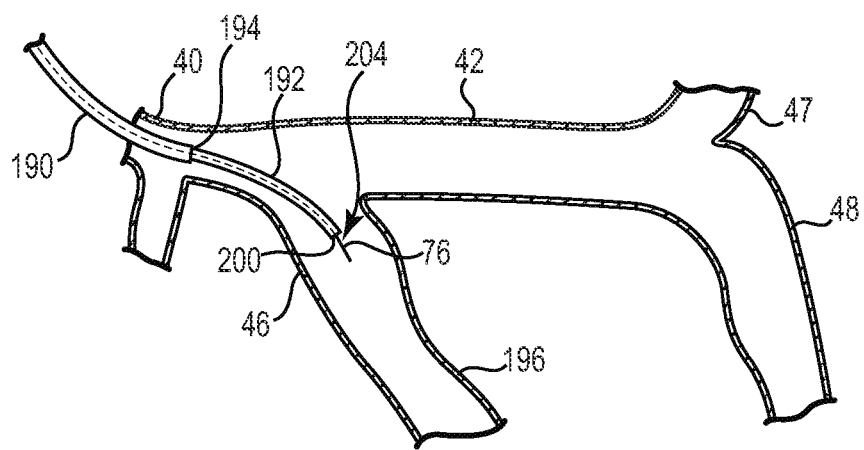
Figure 13:
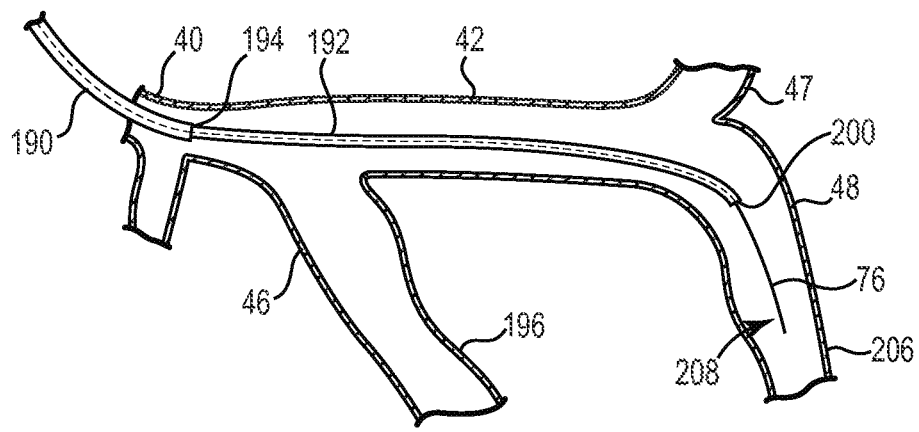
Figure 14:
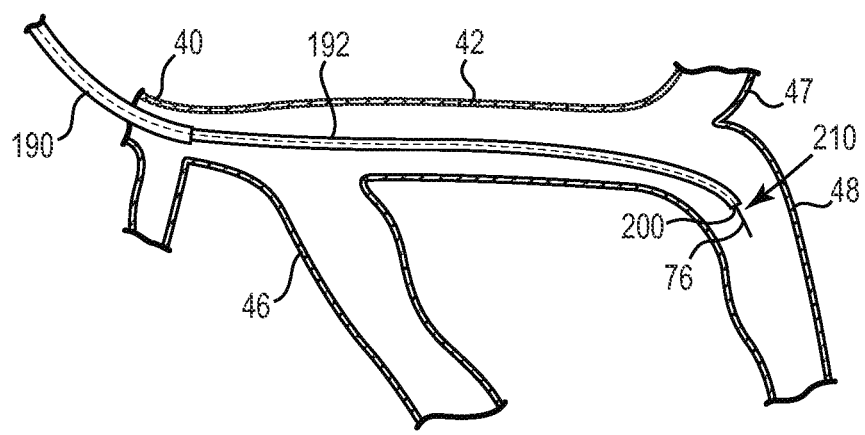

In some embodiments, and as shown in FIG. 11, the mapping guidewire 76 is advanced to a first location 202 within the branch vessel 196, and the signal analyzer 78 is tasked to take one or more electrocardiogram measurements at that location to calculate a timing interval that can be used for determining whether a particular site is optimal, as discussed above. The clinician may then retract the guidewire 76 proximally a distance towards the base 204 of the branch vessel 196 while continuing to take additional electrical measurements within the branch vessel 196, as further shown in FIG. 12. In some embodiments, the measurements can be taken continuously as the guidewire 76 is retracted within the branch vessel 196. In other embodiments, the measurements can be taken at one or more specific locations within the branch vessel 196. In certain embodiments, a roller/stepper mechanism 84 or other suitable servo mechanism can be used to provide the signal analyzer 78 with the precise location of the guidewire 76 within the body at the time the electrical measurements are taken.

If the clinician desires to select a different implantation site, the clinician may then retract the guidewire 76 proximally into the catheter 192 and select another branch vessel for testing. In some embodiments, and as can be further seen in another step in FIG. 13, for example, the catheter 192 carrying the guidewire 76 can be advanced to a second, more lateral branch vessel 206 such as a middle lateral branch vessel, and the guidewire 76 can be again advanced distally beyond the distal end 200 of the catheter 192 to a first location 208 within the second branch vessel 206 for sensing an electrical measurement at that location 208. As can be further seen in another step in FIG. 14, the process of retracting the guidewire 76 proximally towards a base 210 of the branch vessel 206 while taking one or more additional electrical measurements can then be performed within the second branch vessel 206. In some embodiments, the clinician may further deliver pacing pulses to the guidewire electrodes to determine whether a particular pacing site is responsive to pacing stimulus, resulting in activation. If desired, the process of determining other optimal sites can be performed for additional branch vessel(s) within the body.

Figure 15:
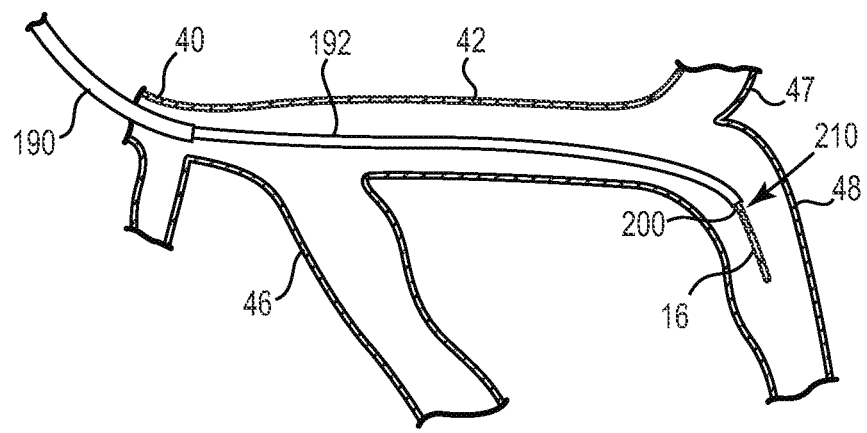

Once a site is selected, and as further shown in another step in FIG. 15, the clinician may next advance a lead 16 over the mapping guidewire 76 to the proposed implantation site. Additional tests may also be performed in conjunction with a pacing system analyzer (PSA) to determine lead characteristics such as capture amplitude, impedance, and so forth. In some embodiments, the mapping guidewire 76 may be used to temporarily pace the heart to determine the pacing threshold associated with that site. The mapping guidewire 76 and catheters 190, 192 can then be removed from the body and the process repeated for any additional leads to be implanted within the body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for selecting a cardiac lead pacing site within a body, comprising:
   inserting a first catheter into the body and cannulating the coronary sinus;
   advancing a second catheter through the first catheter into a first branch vessel in or near the heart;
   advancing a mapping guidewire through the second catheter to a first location within the first branch vessel;
   sensing a plurality of electrocardiogram signals at a plurality of target pacing sites, respectively, while retracting the mapping guidewire in a continuous manner within the first branch vessel, the plurality of electrocardiogram signals sensed with a signal analyzer via an electrode of the mapping guidewire, the electrode of the mapping guidewire retracted along each of the plurality of target pacing sites by a roller mechanism while the roller mechanism provides location feedback information of the electrode to the signal analyzer;
   calculating a plurality of timing interval values based on the plurality of electrocardiogram signals, respectively, each timing interval value calculated as the time between a first deflection and a maximum deflection of a ventricular depolarization of the respective electrocardiogram signal;
   comparing the plurality of timing interval values to a threshold or each other; and
   selecting one of the target pacing sites in the first branch vessel as the cardiac lead pacing site based on the comparison step.

2. The method of claim 1, further comprising sensing a plurality of reference electrocardiogram signals while sensing the plurality of electrocardiogram signals, wherein selecting one of the target pacing sites as the cardiac lead pacing site is further based on the plurality of reference electrocardiogram signals.

3. The method of claim 1, wherein the mapping guidewire comprises a layer of insulation disposed about an electrically conductive solid core wire, a surface of the electrically conductive solid core wire exposed through a window in the layer of insulation.

4. The method of claim 1, further comprising:
   inserting the mapping guidewire into at least one additional branch vessel;
   repeating the steps of sensing, calculating, comparing, and selecting for each of the at least one additional branch vessel to select at least one additional cardiac lead pacing site within the at least one additional branch vessel, respectively.

5. The method of claim 1, further comprising advancing a lead over the mapping guidewire and implanting the lead at the cardiac lead pacing site.

6. The method of claim 1, further comprising providing electrical stimulus therapy to at least one of the plurality of target pacing sites using the mapping guidewire.

7. A method for selecting a cardiac lead pacing site within a body, comprising:
   inserting a first catheter into the body and cannulating the coronary sinus;
   advancing a second catheter through the first catheter;
   advancing a mapping guidewire through the second catheter and into a branch vessel;

sensing a plurality of electrocardiogram signals at a plurality of target pacing sites, respectively, within the branch vessel, the plurality of electrocardiogram signals sensed with a signal analyzer via an electrode of the mapping guidewire, the electrode being moved to each of the plurality of target pacing sites by a roller mechanism that retracts the mapping guidewire in a continuous manner within the branch vessel while the plurality of electrocardiogram signals are sensed at the plurality of target pacing sites and while the roller mechanism provides location feedback information of the electrode to the signal analyzer; and selecting one of the target pacing sites in the branch vessel as the cardiac lead pacing site based on the plurality of electrocardiogram signals.

8. The method of claim 7, further comprising advancing a lead over the mapping guidewire and implanting the lead at the cardiac lead pacing site within the branch vessel.

9. The method of claim 7, further comprising:
determining respective locations of the plurality of target pacing sites from which the plurality of electrocardiogram signals were sensed based on the feedback information.

10. The method of claim 7, further comprising:
calculating a plurality of timing interval values based on the plurality of electrocardiogram signals, respectively, each timing interval value calculated as the time between two deflections of a ventricular depolarization in the respective electrocardiogram signal; and
comparing the plurality of timing interval values to a threshold or each other, wherein the step of selecting one of the target pacing sites as the cardiac lead pacing site is based on the comparison step.

11. The method of claim 10, wherein the two deflections comprise a first deflection and a maximum deflection of the ventricular depolarization.

12. A method for selecting a cardiac lead pacing site within a body, comprising:
inserting a catheter into the body and cannulating the coronary sinus;
advancing a mapping guidewire through the catheter and into a branch vessel, the mapping guidewire including an electrode;
sensing a plurality of electrocardiogram signals at a plurality of target pacing sites, respectively, while retracting the mapping guidewire in a continuous manner within the branch vessel, the plurality of electrocardiogram signals sensed with a signal analyzer via the electrode of the mapping guidewire, the electrode retracted along each of the plurality of target pacing sites by a roller mechanism while the roller mechanism provides location feedback information of the electrode to the signal analyzer;
sensing a plurality of reference electrocardiogram signals with a reference electrode while the plurality of electrocardiogram signals are sensed, respectively;
calculating a plurality of timing interval values based on the plurality of electrocardiogram signals and the plurality of reference electrocardiogram signals, respectively, each timing interval value calculated as the time between a first signal deflection and a peak signal deflection of a ventricular depolarization as indicated by one of the plurality of electrocardiogram signals and one of the plurality of reference electrocardiogram signals;
comparing the plurality of timing interval values to a threshold or each other; and
selecting one of the target pacing sites in the branch vessel as the cardiac lead pacing site based on the comparison step.

13. The method of claim 12, wherein the reference electrode is a surface electrode that is separate from the mapping guidewire.

14. The method of claim 12, wherein the plurality of reference electrocardiogram signals are sensed from the right ventricle.

15. The method of claim 12, wherein the plurality of reference electrocardiogram signals are sensed from the right atrium.

16. The method of claim 12, further comprising advancing a lead over the mapping guidewire and implanting the lead within the branch vessel at the cardiac lead pacing site.

* * * * *